(12) United States Patent
Sahel et al.

(10) Patent No.: US 12,064,181 B2
(45) Date of Patent: Aug. 20, 2024

(54) METHOD OF ANALYZING A VISUAL FIELD OF AN INDIVIDUAL AND A CORRESPONDING OPHTHALMIC LENS

(71) Applicants: SORBONNE UNIVERSITÉ, Paris (FR); ESSILOR INTERNATIONAL, Charenton-le-pont (FR)

(72) Inventors: José-Alain Sahel, Paris (FR); Angelo Arleo, Paris (FR); Anne-Catherine Scherlen, Charenton-le-pont (FR); Delphine Tranvouez-Bernardin, Charenton-le-pont (FR)

(73) Assignees: Essilor International, Charenton-le-pont (FR); Sorbonne Université, Paris (FR)

( * ) Notice: Subject to any disclaimer, the term of this patent is extended or adjusted under 35 U.S.C. 154(b) by 285 days.

(21) Appl. No.: 16/954,720

(22) PCT Filed: Dec. 21, 2017

(86) PCT No.: PCT/IB2017/001751
§ 371 (c)(1),
(2) Date: Jun. 17, 2020

(87) PCT Pub. No.: WO2019/122945
PCT Pub. Date: Jun. 27, 2019

(65) Prior Publication Data
US 2021/0085172 A1 Mar. 25, 2021

(51) Int. Cl.
*A61B 3/02* (2006.01)
*A61B 3/00* (2006.01)
(Continued)

(52) U.S. Cl.
CPC ............ *A61B 3/024* (2013.01); *A61B 3/0041* (2013.01); *A61B 3/113* (2013.01)

(58) Field of Classification Search
CPC ....... A61B 3/024; A61B 3/1225; A61B 3/032; A61B 3/103; A61B 3/14; A61B 3/113; A61B 3/02; A61B 3/18; A61B 3/1015
(Continued)

(56) References Cited

U.S. PATENT DOCUMENTS

| 4,971,434 A | 11/1990 | Ball |
| 5,801,810 A | 9/1998 | Roenker |

(Continued)

FOREIGN PATENT DOCUMENTS

| CN | 104335103 | 2/2015 |
| CN | 106455967 | 2/2017 |

(Continued)

OTHER PUBLICATIONS

Durand, et al., "Eye Privileged Visual Processing of the Straight-Ahead Direction in Humans," Journal of Vision, 12(6): 34, 1-13, 2012.

(Continued)

*Primary Examiner* — Dawayne Pinkney
(74) *Attorney, Agent, or Firm* — Norton Rose Fulbright US LLP

(57) ABSTRACT

A method of analyzing a visual field of an individual comprises the following steps: —measuring (S4) a first visual field (VF1) of said individual for a first set of oculo-postural parameters of said individual when said individual performs a first task; —measuring (S6) at least one additional visual field (VFi) of said individual for one additional set of said oculo-postural parameters of said individual when said individual performs an additional task; —determining (S8) a functional visual space based on said first visual field (VF1) and said at least one additional visual field (VFi), said functional visual space being an envelope of said first visual field and said at least one additional visual (Continued)

field. The additional task differs from said first task and/or said additional set of oculo-postural parameters differs from said first set of oculo-postural parameters. A corresponding ophthalmic lens is also proposed.

15 Claims, 1 Drawing Sheet

(51) Int. Cl.
*A61B 3/024* (2006.01)
*A61B 3/10* (2006.01)
*A61B 3/113* (2006.01)

(58) Field of Classification Search
USPC ....... 351/246, 221–224, 200, 203, 205, 206, 351/209–211, 239, 243–245
See application file for complete search history.

(56) References Cited

U.S. PATENT DOCUMENTS

| | | | |
|---|---|---|---|
| 6,364,486 B1 | 4/2002 | Ball et al. | |
| 9,033,509 B2 | 5/2015 | Fateh | |
| 10,182,715 B2* | 1/2019 | Donaldson | A61B 3/0025 |
| 10,231,615 B2* | 3/2019 | Fateh | A61B 3/005 |
| 2004/0057013 A1 | 3/2004 | Cappo et al. | |
| 2008/0278682 A1* | 11/2008 | Huxlin | A61H 5/00 |
| | | | 351/203 |
| 2011/0205493 A1 | 8/2011 | De la Rosa | |
| 2012/0300032 A1 | 11/2012 | Ookoba | |
| 2015/0131056 A1 | 5/2015 | Paille et al. | |
| 2015/0342454 A1* | 12/2015 | Foster | A61B 3/032 |
| | | | 351/246 |
| 2016/0038020 A1 | 2/2016 | Narasimha et al. | |
| 2017/0181617 A1 | 6/2017 | Bonnin et al. | |
| 2019/0142270 A1* | 5/2019 | Monhart | A61B 3/1005 |
| | | | 351/209 |
| 2022/0160223 A1* | 5/2022 | Bradley | G02B 27/0176 |

FOREIGN PATENT DOCUMENTS

| | | | |
|---|---|---|---|
| EP | 0502984 | 9/1992 | |
| EP | 1503348 | 2/2005 | |
| JP | 2014171586 A | 9/2014 | |
| WO | WO 1991/007908 | 6/1991 | |
| WO | WO 1996/034555 | 11/1996 | |
| WO | WO 2013/078462 | 5/2013 | |
| WO | WO 2013/123587 | 8/2013 | |
| WO | WO 2017/182596 | 10/2017 | |
| WO | WO-2018056791 A1 * | 3/2018 | A61H 5/00 |
| WO | WO 2019/122945 | 6/2019 | |

OTHER PUBLICATIONS

International Search Report and Written Opinion Issued in Corresponding PCT Patent Application No. PCT/IB2017/001751, dated Sep. 12, 2018.

Nakashima & Shioiri, "Why Do We Move Our Head to Look at an Object in Our Peripheral Region? Lateral Viewing Interferes with Attentive Search," *PLOS One*, 9(3): e92284, 2014.

Reed-Jones, et al., "Is the Size of the Useful Field of View Affected by Postural Demands Associated with Standing and Stepping?" *Neuroscience Letters*, 566: 27-31, 2014.

Ringer, et al., "A Novel Approach to Measuring the Useful Field of View in Simulated Real-World Environments Using Gaze Contingent Displays: The GC-UFOV," Journal of Vision 15(12): 878, 2015.

Office Action issued in corresponding Chinese Application No. 201780097475.9, dated Apr. 29, 2023 (English translation).

* cited by examiner

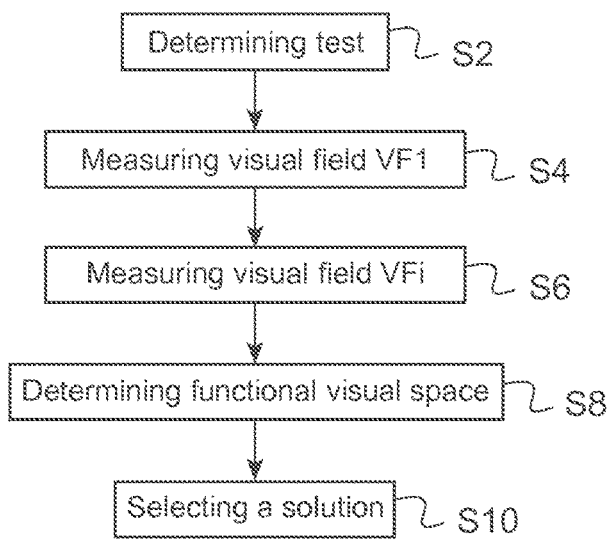
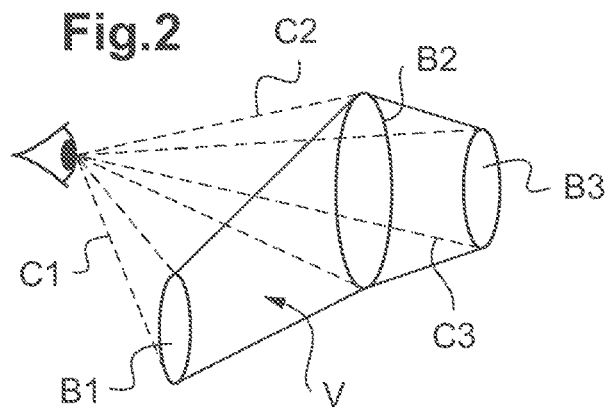
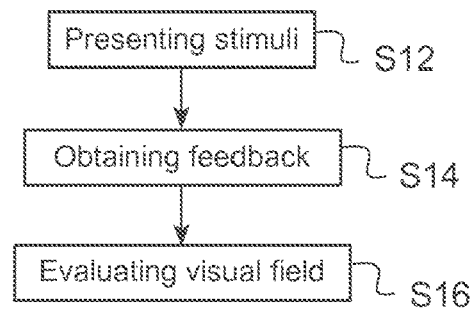
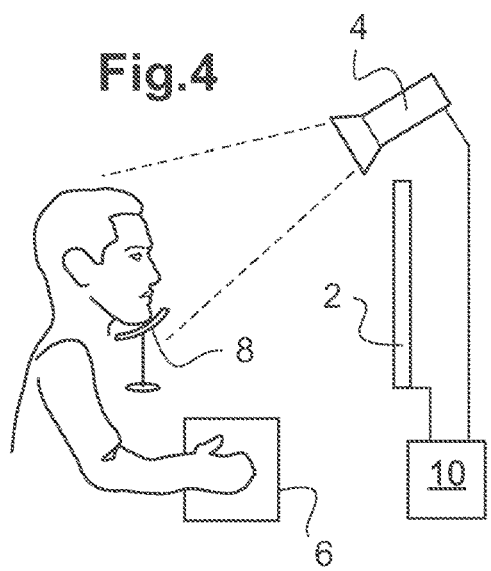
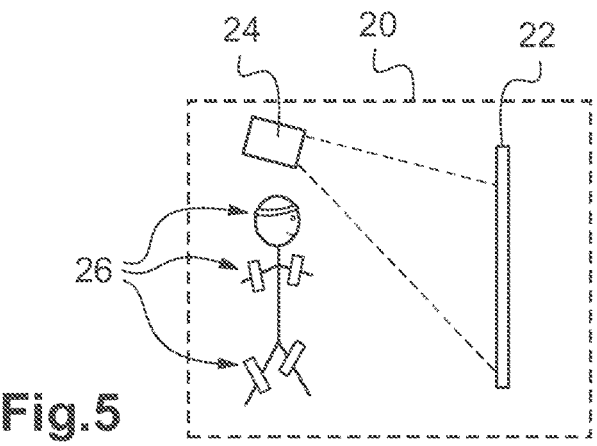

METHOD OF ANALYZING A VISUAL FIELD OF AN INDIVIDUAL AND A CORRESPONDING OPHTHALMIC LENS

CROSS-REFERENCE TO RELATED APPLICATIONS

This application is a national phase application under 35 U.S.C. § 371 of International Application No. PCT/IB2017/001751 filed 21 Dec. 2017, the entire contents of which is specifically incorporated by reference herein without disclaimer.

TECHNICAL FIELD OF THE INVENTION

The invention relates to systems for testing vision.
More precisely the invention relates to a method of analyzing the visual field of an individual and to a corresponding ophthalmic lens.

BACKGROUND INFORMATION AND PRIOR ART

It is known to measure the useful field of view (UFOV) of an individual by testing his/her response to stimuli displayed on a screen.
This measured useful field of view is meant to represent areas where the individual is able to locate stimuli without moving the head or the eyes.
Such a test is thus performed for a given posture of the individual, generally sitting in front of the screen, and for a given fixation (i.e. gaze orientation).
Such specific measurement conditions greatly differ from the conditions the individual may come across in everyday life.
As a consequence, the useful field of view defined above may reveal inadequate to understand the actual needs of the individual, for instance when it comes to defining an ophthalmic lens best suited to correct the individual's ametropia.

SUMMARY OF THE INVENTION

In this context, the invention provides a method of analyzing a visual field of an individual comprising the following steps:
measuring a first visual field of said individual for a first set of oculo-postural parameters of said individual when said individual performs a first task;
measuring at least one additional visual field of said individual for one additional set of said oculo-postural parameters of said individual when said individual performs an additional task;
determining a functional visual space based on said first visual field and said at least one additional visual field, said functional visual space being an envelope of said first visual field and said at least one additional visual field;
wherein said additional task differs from said first task and/or said additional set of oculo-postural parameters differs from said first set of oculo-postural parameters.

Such a functional visual space thus gives a representation of the visual field which accounts for several postures or several tasks the individual may effect in everyday life. The functional visual space can thus be advantageously used when seeking to provide optical solutions which best fit the individual's visual field in everyday life.

The proposed method may also include any of the following features:
said first or additional visual field is defined by a base surface of a cone;
said cone comprises an apex located on an eye of said individual;
said cone comprises a height defined by the task performed by the individual;
the functional visual space is defined by a volume concatenation between said measured visual fields;
said first visual field and/or said second visual field includes a temporal component;
said oculo-postural parameters include parameters defining: an eye orientation of said individual, or an eye orientation temporal evolution of said individual, or a head orientation of said individual, or a head orientation temporal evolution of said individual, or a posture of said individual, or a posture temporal evolution of said individual;
a device for detecting the eye orientation of said individual is used during the steps of measuring;
a device for detecting the head orientation of said individual is used during the steps of measuring;
a device for detecting a posture of said individual is used during the steps of measuring;
the steps of measuring include displaying stimuli intended for the individual, for instance using a screen;
a sequence displayed (e.g. on the screen) is determined based on a task to be tested;
the functional visual space is further defined by a plurality of weights respectively associated with the measured visual fields;
the method comprises a step of determining a lens design based on said determined functional visual space;
the method comprises a step of selecting a training program based on said determined functional visual space;
the method comprises a step of selecting a visuo-spatial re-education protocol based on said determined functional visual space;
the method comprises estimating an effect of an ophthalmological treatment based on said determined functional visual space.

The invention also provides an ophthalmic lens intended to be worn by an individual, wherein the lens has a design determined based on a functional visual space determined by the method proposed above.

DETAILED DESCRIPTION OF EXAMPLE(S)

The invention will be better understood in light of the appended drawings, where:
FIG. 1 illustrates the main steps of a method embodying the invention;
FIG. 2 schematically shows a possible representation of a measured visual field;
FIG. 3 illustrates the main steps of a possible method used for measuring a visual field;
FIG. 4 schematically shows a possible system for measuring a visual field; and
FIG. 5 schematically shows another possible system for measuring a visual field.
FIG. 1 illustrates the main steps of a method of analyzing a visual field of an individual.
This method begins with a step S2 of determining features of the visual test to be performed depending on the targeted task, on an eye/head/body coordination associated with the targeted task and on parameters relating to the individual undergoing the visual test.

The targeted task is generally a task carried out in everyday life, such as reading, walking, etc.

In step S2, for instance, parameters defining the visual stimuli presented to the individual (as further explained below) may be determined depending on the targeted task. This is because the individual tends to use his/her visual capabilities in different manners depending on the task in everyday life he/she is performing.

These parameters defining the visual stimuli may include:
- type of stimuli to identify (e.g. one or several among: meshes, letters, symbols, faces, scenes, objects);
- characteristics of the stimuli (e.g. one or several among: size, spatial frequency or acuity, contrast, motion, orientation, color, brightness);
- position(s) in the visual field: central, nearly central, peripheral, in the lower visual field, in the upper visual field, left, right (several positions may be used jointly to characterize divided attention);
- number of stimuli;
- inclusion of noise in the scene or not (noise in the scene makes it possible to characterize selective attention);
- focusing plane of the stimuli (e.g. one or several among: far vision, intermediate vision, near vision, another distance).

Several stimuli or objects may be presented simultaneously, each stimulus or object then being possibly defined according to one or several of the parameters listed above.

The test to be performed is also defined by the eye/head/body coordination to be considered depending on the targeted task.

An eye/head/body coordination defines the respective positions of the eye, the head and the body.

The visual test may be performed in several possible distinct conditions, such as:
- a fixed straight state;
- a fixed offset state (defined for instance by the location and amplitude of the offset compared to the straight state and/or using angles specifying the concerned direction with respect to the straight state);
- a moving state (defined for instance by a starting position with respect to the straight state, a direction, a speed, an amplitude of movement and a type of movement).

It may be noted that, for each state, the position of the eye, the position of the head and the position of the body are defined and may in addition be moving (for the moving state).

As noted above, features of the visual test are also determined in step S2 based on parameters relating to the individual undergoing the test, such as:
- whether the individual wears an optical correction or not, and possibly the type of correction (e.g. spherical or progressive lens);
- the quality of binocular vision;
- cognitive skills (such as determined for instance using the Mini-Mental State Examination);
- the individual's ametropia;
- the individual's age (the moment and/or duration of the presentation of the stimuli being for instance adapted depending on the individual's age, as reaction time is longer for senior people);
- motor skills (oculomotricity, head and/or body motions, characteristics of body segment coordination).

Oculomotricity can be characterized for instance by one or several of the following parameters: fixation stability, offset fixation, nystagmus, fixation disparity, convergence, saccade amplitude, pursuit, vergence and divergence of extra ocular muscles.

Head and body motions can be characterized for instance by one or several of the following parameters: tremor (parkinsonism), posture stability, loss of balance, walking speed.

Body segment coordination may be characterized for instance by one or several of the following parameters: the number of segments involved, their rigidity, the amplitude and speed of their motions.

The method of FIG. 1 then includes a step S4 of measuring a first visual field VF1 of the individual using (part of) the test defined as per the step S2 described above.

This measurement is performed for a first set of oculo-postural parameters of said individual while said individual performs a first task (such as a task of everyday life as explained above).

An example of how this measurement can be implemented is described below referring to FIG. 3.

The method of FIG. 1 also includes a step S6 of measuring an additional visual field VFi of the individual for an additional set of oculo-postural parameters while said individual performs an additional task.

The additional task differs from said first task and/or said additional set of oculo-postural parameters differs from said first set of oculo-postural parameters.

Several distinct measurements of such additional visual fields VFi may be performed, each time with distinct oculo-postural parameters and/or while performing distinct tasks.

An example of how each of these additional measurements can be implemented is described below referring to FIG. 3.

A measured visual field (here the first visual field VF1 or the additional visual field VFi) may be defined in space by a solid angle, or, in practice, by two angles $\Theta_x$, $\Theta_y$ respectively defining the angular extension of the measured visual field in two orthogonal directions (e.g. horizontally and vertically).

A measured visual field may also be defined by a volume, for instance a cone having an apex located on a eye of the individual and a height z corresponding to the task performed by the individual (the height z being for instance equal to the distance at which vision is tested, either for far vision, intermediate vision or near vision as noted above).

In a possible embodiment, the volume defining the measured visual field may be defined by a plurality of frusto-conical portions joining the respective bases B1, B2, B3 of several cones C1, C2, C3 as just mentioned, as schematically shown in FIG. 2.

In this example, the cone C1 corresponds to near vision, the cone C2 corresponds to intermediate vision and the cone C3 corresponds to far vision.

Taking into account several types of vision makes it possible to characterize how visual and attention capabilities of the individual evolve depending on the activity (or task) and associated distance(s) involved with respect to the individual. It may be noted in this respect that, even when the individual gazes in a particular direction of fixation at a particular distance (such as watching the road in front of him when driving), he/she may react to stimuli in other directions of fixation and/or at another distance (such as inside the vehicle, e.g. on the dashboard).

A measured visual field may also include a temporal component. In practice for instance, the spatial component of the visual field (represented by a solid angle or a volume as explained above) may be determined for several points in time, thereby describing the visual and cognitive processing time of the individual.

A measured visual field may also include indications as to a threshold for discriminating stimuli. This threshold may be determined by displaying stimuli having distinct extents. In practice, a threshold may be indicated for each of a plurality of directions within the visual field. According to possible embodiments however, such a threshold indication is not included in the measured visual field, but the extent (or size) of displayed stimuli is determined based on the individual's skills and/or based on the activity under test.

After several visual fields VF1, VFi are measured as just described, the method of FIG. 1 includes a step S8 of determining a functional visual space based on said first visual field VF1 and said additional visual field(s) VFi.

The functional visual space considered here is defined as an envelope of the first visual field and the additional visual field(s), i.e. a set of points which are included in either one of the first visual field and additional visual field(s).

The functional visual space may in practice be determined as a volume concatenation between the first visual field VF1 and each of the additional visual field(s) VFi.

According to a possible implementation, distinct weights may be attributed to the various measured visual fields VF1, VFi (for instance depending on the oculo-postural parameters or task involved for measurement of the concerned visual field VF1, VFi, compared to targeted oculo-postural parameters or task) to further define the functional visual space.

The method of FIG. 1 then includes a step S10 of selecting a solution based on the determined functional visual space, i.e. in practice based on parameters or data characterizing the functional visual space determined in step S8.

Selecting a solution may include determining an optical article to be worn by the individual who underwent the above described test.

Selecting a solution may for instance include determining a lens design based on said determined functional visual space.

In particular, the design of a progressive addition lens (PAL) may be determined based on the determined functional visual space.

By defining the individual's visual field in one or several tasks encountered in everyday life (with object distance associated to each concerned task), the functional visual space can be used to determine where areas providing correction should be located on the progressive addition lens and, possibly, where respective corrections corresponding to the various object distances considered (e.g. correction for near vision or correction for intermediate vision or correction for far vision) should be provided on the progressive addition lens.

Selecting a solution may also include determining the design of a filter to be deposited on a lens to be worn by the individual.

Such a filter may be deposited in areas of the lens corresponding to regions of space where optical noise (such as possibly generated by a progressive addition lens) would lower visual capabilities of the individual according to the determined functional visual space (the spatial and/or temporal components of the functional visual space comprising for instance in this case data indicating poor individual's reactions during tests involving spatial noise).

Selecting a solution may include selecting a training program based on said determined functional visual space.

Such a training program may then be proposed to the individual to improve his/her visual capabilities, in particular in terms of visual field.

In particular, the determined functional visual space may be used to select at least an appropriate visuo-spatial re-education protocol.

Such a visuo-spatial re-education protocol may for instance aim at optimizing the individual's eye/head/body coordination to compensate for the loss in the visual field and/or at improving the individual's ability to extract relevant visual information to find his/her way in space.

Selecting a visuo-spatial re-education protocol may also involve quantifying the effect of the eye/head/body coordination on the resulting useful field of view (to select a re-education protocol directed to improving this coordination in case of negative effect).

In this goal, the function visual space may be determined as explained above in various distinct conditions involving more or less degrees of freedom in the eye/head/body coordination such that the effect of the eye/head/body coordination may be estimated and a re-education protocol aiming at improving the eye/head/body coordination may possibly be proposed to the individual.

According to another possible embodiment, the determined functional visual space may be used for estimation and follow-up of an ophthalmological treatment.

This is the case for instance when the individual is a patient suffering from a visual pathology, such as age-related macular degeneration or glaucoma.

Visual pathologies may indeed result in loss of visual acuity, loss of sensitivity to contrasts, loss of stability in ocular fixation, loss in the extent of the visual field.

Such disabilities then have consequences on performances as regards oculomotor explorations and identifications, reading, spatial orientation and navigation, face recognition.

In view of this, the functional visual space may advantageously be determined before and/or all along the ophthalmological treatment meant to treat the concern visual pathology.

In particular, the determination of the functional visual field (including before starting the ophthalmological treatment) as described above makes it possible:

to estimate the effect of the visual pathology on the data resulting from the estimation of the functional visual field as described above;

to compare these data with corresponding data obtained for healthy subjects so as to estimate the level of loss of capabilities to estimate the effect of the ophthalmological treatment by determining anew the functional visual space (e.g. at some specific steps of the treatment);

to orientate the further ophthalmological treatment (i.e. to select a further step of the ophthalmological treatment or another ophthalmological treatment) or to select a visuo-spatial re-education program or protocol (as mentioned above) based on data defining the functional visual space (possibly with a view to obtain a target value of the functional visual space).

FIG. 3 illustrates the main steps of a method for measuring a visual field. This method is described below as possibly implemented in two distinct systems for measuring the visual field (respectively shown in FIGS. 4 & 5).

A first possible system for measuring a visual field is shown in FIG. 4 and includes a display screen 2, a (video) camera 4 directed to the individual's face, a user interface 6 (such as a joystick, a keyboard or a tactile screen), a device 8 for imposing a position of a head or body segment of the individual (such as a chin rest) and a control unit 10.

The display screen 2 is usable for displaying stimuli intended for the individual, as further explained below.

The camera 4 is usable as an eye tracker, i.e. as a device for detecting the eye orientation (or gaze direction) of the individual.

A second possible system for measuring a visual field is a user experience room 20, as shown schematically in FIG. 5. This user experience room 20 includes a screen 22, a projection unit 24 adapted to project an image onto the screen 22 and sensors 26 respectively affixed to various head or body segments of the individual.

Sensors 26 thus forms a device for detecting a posture of the individual.

As an alternative to these two possible systems, use can be made of an augmented reality helmet, possibly including an eye tracker and a unit adapted to determine the position and/or orientation of the helmet (such as accelerometers and/or gyrometers). This unit is thus adapted to detect the head orientation of the individual when the individual wears the helmet.

The method of FIG. 3 comprises a step S12 of presenting to the individual visual stimuli, including one of several target(s) to be identified by the individual.

The stimuli are for instance presented (under the control of a control unit such as control unit 10) by being displayed on a screen (such as the display screen 2 of FIG. 4 or the screen 22 of FIG. 5) or, as an alternative, in the augmented reality helmet mentioned above.

The type of stimuli to be displayed, their time of presentation (display) and their duration of presentation (display) are determined in accordance with step S2 described above.

In particular, the sequence of stimuli to be displayed on the screen may be determined based on a task to be tested.

The individual's feedback to the stimuli presented to him/her are obtained in a step S14, for instance through a user interface (such as user interface 6 of FIG. 4) or by detecting specific movements of the individual (for instance at least one of the sensors 26 of FIG. 5).

The individual's feedback is received by a control unit (such as control unit 10 of FIG. 4) which determines the individual's ability to react to a specific stimulus (e.g. to identify a particular target among presented stimuli).

The control unit (e.g. control unit 10) is thus adapted to evaluate the individual's visual field at step S16 (in practice after repeating several times the presentation of stimuli of step S12 and the receipt of a corresponding feedback from the individual as per step S14).

The measurement of the visual field by the method of FIG. 3 just described occurs for a given set of oculo-postural parameters, possibly while the individual performs a particular task.

These oculo-postural parameters may include parameters defining:
- an eye orientation of said individual, and/or
- an eye orientation temporal evolution of said individual, and/or
- a head orientation of said individual, and/or
- a head orientation temporal evolution of said individual, and/or
- a posture of said individual, and/or
- a posture temporal evolution of said individual.

Each of the oculo-postural parameters considered may either be fixed by the conditions in which the test is carried out (e.g. using the chin rest 8 of FIG. 4) or measured in real time during the test, for instance using an eye tracker to determine gaze direction (thanks to the camera 4 in the embodiment of FIG. 4 or the eye tracker in the augmented reality helmet in the variant proposed above), or using sensors 26 for measuring position and/or motion of head or body segments in the embodiment of FIG. 5.

The control unit mentioned above (e.g. control unit 10 in the context of FIG. 4) may thus record in practice (i.e. store in a memory) the oculo-postural parameters measured as just mentioned in association with the measured visual field.

The invention claimed is:

1. A method of analyzing a visual field of an individual comprising the following steps:
    measuring a first visual field of said individual for a first set of oculo-postural parameters of said individual when said individual performs a first task;
    measuring at least one additional visual field of said individual for one additional set of said oculo-postural parameters of said individual when said individual performs an additional task;
    determining a functional visual space based on said first visual field and said at least one additional visual field, said functional visual space being an envelope wherein said envelope is a set of points including points included in said first visual field and points included in said at least one additional visual field;
    wherein said additional task differs from said first task or said additional set of oculo-postural parameters differs from said first set of oculo-postural parameters.

2. The method according to claim 1, wherein said first or additional visual field is defined by a base surface of a cone, wherein said cone comprises an apex located on an eye of said individual and said cone comprises a height z equal to the distance at which vision is tested by the task performed by the individual.

3. The method according to claim 1, wherein the functional visual space is defined by a volume concatenation between said measured visual fields.

4. The method according to claim 1, wherein said first visual field includes a temporal component.

5. The method according to claim 1, wherein said oculo-postural parameters include parameters defining:
    an eye orientation of said individual, or
    an eye orientation temporal evolution of said individual, or
    a head orientation of said individual, or
    a head orientation temporal evolution of said individual, or
    a posture of said individual, or
    a posture temporal evolution of said individual.

6. The method according to claim 5, wherein a device for detecting the eye orientation of said individual is used during the steps of measuring.

7. The method according to claim 5, wherein a device for detecting the head orientation of said individual is used during the steps of measuring.

8. The method according to claim 5, wherein a device for detecting a posture of said individual is used during the steps of measuring.

9. The method according to claim 1, wherein the steps of measuring include displaying stimuli intended for the individual.

10. The method according to claim 9, wherein a sequence displayed is determined based on a task to be tested.

11. The method according to claim 1, wherein the functional visual space is further defined by a plurality of weights respectively associated with the measured visual fields.

12. The method according to claim 1, comprising a step of determining a lens design based on said determined functional visual space.

13. The method according to claim 1, comprising a step of selecting a training program based on said determined functional visual space.

14. The method according to claim 1, comprising a step of selecting a visuo-spatial re-education protocol based on said determined functional visual space.

15. An ophthalmic lens intended to be worn by an individual, wherein the lens has a design determined based on a functional visual space based on a first visual field and at least one additional visual field, said functional visual space being an envelope wherein said envelope is a set of points including points included in said first visual field and points included in said at least one additional visual field.

* * * * *